(12) United States Patent
Hiereth et al.

(10) Patent No.: US 7,503,701 B2
(45) Date of Patent: Mar. 17, 2009

(54) SYSTEMS AND METHODS FOR CLEANING AN OPTICAL FIBRE

(75) Inventors: Werner Hiereth, Gilching (DE); Oliver Durian, Bobingen (DE)

(73) Assignee: Dornier MedTech Laser GmbH, Wessling (DE)

( * ) Notice: Subject to any disclaimer, the term of this patent is extended or adjusted under 35 U.S.C. 154(b) by 0 days.

(21) Appl. No.: 11/406,042

(22) Filed: Apr. 18, 2006

(65) Prior Publication Data

US 2007/0014521 A1 Jan. 18, 2007

(30) Foreign Application Priority Data

Apr. 18, 2005 (DE) ........................ 10 2005 017 798

(51) Int. Cl.
G02B 6/36 (2006.01)
G02B 6/00 (2006.01)

(52) U.S. Cl. .............................. 385/53; 385/55; 385/85; 385/134

(58) Field of Classification Search .................... 385/53, 385/55, 85, 88, 134
See application file for complete search history.

(56) References Cited

U.S. PATENT DOCUMENTS

| 48,847 | A | | 7/1865 | Smith |
|---|---|---|---|---|
| 4,261,345 | A | * | 4/1981 | Yamaguchi .................. 600/132 |
| 4,592,353 | A | | 6/1986 | Daikuzono |
| 4,693,244 | A | | 9/1987 | Daikuzono |
| 4,722,337 | A | | 2/1988 | Losch |
| 4,736,743 | A | | 4/1988 | Daikuzono |
| 4,822,997 | A | | 4/1989 | Fuller |
| 4,907,588 | A | | 3/1990 | Burston |
| 5,071,222 | A | | 12/1991 | Laakmann |
| 5,098,427 | A | | 3/1992 | Hessel |
| 5,112,328 | A | | 5/1992 | Taboada |
| 5,139,494 | A | | 8/1992 | Freiberg |
| 5,154,708 | A | | 10/1992 | Long |

(Continued)

FOREIGN PATENT DOCUMENTS

DE 84 16 748 U1 8/1984

(Continued)

OTHER PUBLICATIONS

Author: Abou-Jawde, R. et al. Title: An Overview of Targeted Treatments in Cancer Publ: *Clinical Therapeutics* vol./Iss: 25 (8) pp. 2121-2137 Date: 2003.

(Continued)

*Primary Examiner*—Hemang Sanghavi
(74) *Attorney, Agent, or Firm*—King & Spalding LLP

(57) ABSTRACT

The invention relates to an optical fibre with a connector piece that has a recess, such as a bore hole, for instance, for accommodating the optical fibre, wherein a fluid channel (18, 14) is provided that begins at the end of the recess and through which a fluid can pass. The invention furthermore relates to an optical fibre with a plug with a gripping piece that has two end openings, wherein the fibre enters into the gripping piece in one end opening and the light of the fibre or the fibre can exit from the gripping piece through the other end opening, wherein the end openings (15, 16) of the gripping piece (2) are interconnected in a way allowing throughflow.

12 Claims, 1 Drawing Sheet

U.S. PATENT DOCUMENTS

| | | | |
|---|---|---|---|
| 5,300,066 A | 4/1994 | Manoukian | |
| 5,360,447 A | 11/1994 | Koop | |
| 5,409,537 A | 4/1995 | Poullos | |
| 5,416,878 A | 5/1995 | Bruce | |
| 5,454,808 A | 10/1995 | Koop | |
| 5,490,849 A | 2/1996 | Smith | |
| 5,520,681 A | 5/1996 | Fuller | |
| 5,535,399 A | 7/1996 | Blitz | |
| 5,540,676 A | 7/1996 | Freiberg | |
| 5,607,420 A | 3/1997 | Schuman | |
| 5,681,307 A | 10/1997 | McMahan | |
| 5,688,263 A | 11/1997 | Hauptmann | |
| 5,693,043 A | 12/1997 | Kittrell et al. | |
| 5,738,679 A | 4/1998 | Daikuzono | |
| 5,742,718 A | 4/1998 | Harman | |
| 5,841,562 A | 11/1998 | Rangwala | |
| 5,860,972 A | 1/1999 | Hoang | |
| 5,872,618 A | 2/1999 | Nagayama | |
| 5,908,417 A | 6/1999 | Miller | |
| 5,951,543 A | 9/1999 | Brauer | |
| 5,957,915 A | 9/1999 | Trost | |
| 5,971,755 A | 10/1999 | Liebermann | |
| 6,022,345 A | 2/2000 | Miller | |
| 6,086,366 A | 7/2000 | Mueller | |
| 6,092,722 A | 7/2000 | Heinrichs | |
| 6,162,218 A | 12/2000 | Elbrecht | |
| 6,193,711 B1 | 2/2001 | Connors | |
| 6,270,491 B1 | 8/2001 | Toth | |
| 6,273,885 B1 | 8/2001 | Koop | |
| 6,377,591 B1 | 4/2002 | Hollister | |
| 6,477,426 B1 | 11/2002 | Fenn et al. | |
| 6,567,582 B1 * | 5/2003 | Rizoiu et al. | 385/25 |
| 7,114,855 B2 * | 10/2006 | Wittrisch | 385/55 |
| 7,215,864 B1 * | 5/2007 | Qian et al. | 385/134 |
| 2002/0073082 A1 | 6/2002 | Duvillier | |
| 2002/0081080 A1 | 6/2002 | Balle-Petersen | |
| 2002/0183811 A1 | 12/2002 | Irwin | |
| 2004/0037498 A1 | 2/2004 | Thiele | |
| 2005/0013551 A1 * | 1/2005 | Hung | 385/88 |
| 2005/0105859 A1 * | 5/2005 | Gerhard | 385/85 |
| 2006/0122281 A1 | 6/2006 | Escandon et al. | |

FOREIGN PATENT DOCUMENTS

| | | |
|---|---|---|
| DE | 90 13 085.5 | 1/1991 |
| DE | 40 13 455 A1 | 10/1991 |
| DE | 40 25 851 C2 | 2/1992 |
| DE | 42 16 254 C2 | 8/1994 |
| DE | 42 29 566 C2 | 10/1994 |
| DE | 195 34 590 A1 | 3/1997 |
| DE | 196 29 646 C2 | 1/1998 |
| DE | 197 29 978 A1 | 1/1999 |
| DE | 692 29 128 T2 | 8/1999 |
| DE | 100 09 004 A1 | 10/2001 |
| DE | 101 06 297 A1 | 1/2002 |
| EP | 0 325 836 A | 8/1989 |
| EP | 0 433 464 B1 | 6/1991 |
| EP | 0 473 987 A1 | 11/1992 |
| EP | 0 514 258 A1 | 11/1992 |
| EP | 0 404 968 A | 11/1994 |
| EP | 0 292 622 | 12/1996 |
| JP | 03033808 A * | 2/1991 |
| WO | WO 93/21841 | 11/1993 |
| WO | WO 99/15237 A1 | 4/1999 |

OTHER PUBLICATIONS

Author: Bronchud, M. et al. Title: Selecting the Right Targets for Cancer Therapy Publ: *Principles of Molecular Oncology* pp. 3-27 Date: 2000.

Author: D'Amico, A. Title: Radiation and Hormonal Therapy for Locally Advanced and Clinically Localized Prostate Cancer Publ: *Urology* vol./Iss: 58 (Suppl. 2A) pp. 78-82 Date: 2001.

Author: Douwes, F. et al. Title: Neoadjuvant Hormone Ablation before HIFU Treatment of Localized Prostate Cancer Publ: *Alternative and Complementary Therapies* vol./Iss: 18 (Suppl. 1) pp. A43 Date: Nov. 2004.

Author: Hua, L. et al. Title: High Intensity Focused Ultrasound Combined with Endocrine Therapy in Treating Prostate Cancer Publ: *National Journal of Andrology* vol./Iss: 11(3) pp. Abstract Date: Mar. 2005.

Author: Hurwitz, M. et al. Title: Feasibility and Patient Tolerance of a Novel Transrectal Ultrasound Hyperthermia System for Treatment of Prostate Cancer Publ: *International Journal of Hyperthermia* vol./Iss: 17(1) pp. 31-37 Date: 2001.

Author: Lein, M. et al. Title: Laser-Induced Hyperthermia in Rat Prostate Cancer: Role of Site of Tumor Implantation Publ: *Urology* vol./Iss: 56 pp. 167-172 Date: 2000.

Author: Marberger, M. et al. Title: Energy-Based Ablative Therapy of Prostate Cancer: High Intensity Focused Ultrasound and Cryoablation Publ: *Current Opinion in Urology* vol./Iss: 17 pp. 194-199 Date: 2007.

Author: Strohmaier, W. et al. Title: Influence of Transrectal Hyperthermia on Prostate-Specific Antigen in Prostatic Cancer and Benign Prostatic Hyperplasia Publ: *Urologia Internationalis* vol./Iss: 51(I) abstract pp. 28-31 Date: 1993.

Author: Thueroff, S. et al. Title: Neoadjuvant Hormone Ablation before HIFU Treatment of Localized Prostate Cancer Publ: *Journal of Endourology* vol./Iss: 18(Suppl 1) pp. A43 Date: Nov. 2004.

Author: Trachtenberg, J. et al. Title: Microwave Thermoablation for Localized Prostate Cancer after Failed Radiation Therapy: Role of Neoadjuvant Hormonal Therapy Publ: *Molecular Urology* vol./Iss: 3(3) pp. 247-251 Date: 1999.

* cited by examiner

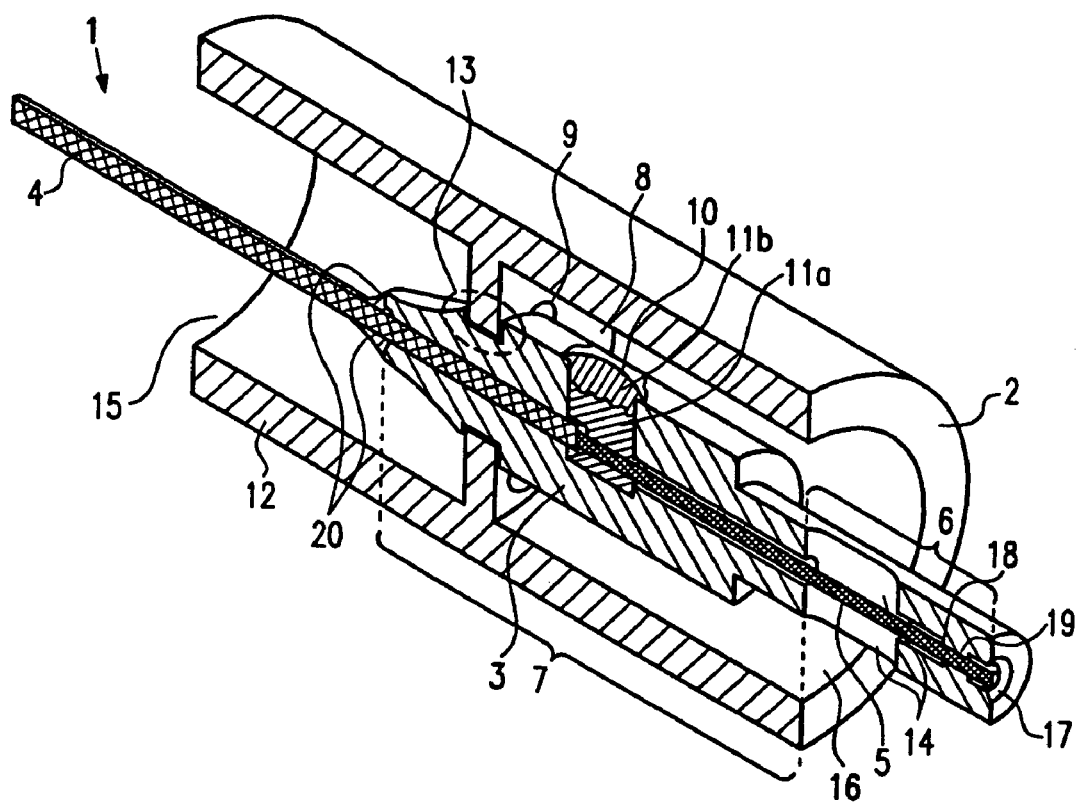

SYSTEMS AND METHODS FOR CLEANING AN OPTICAL FIBRE

The invention relates to an optical fibre with a connector piece.

Optical fibres of this kind are used in medical technology for guiding (laser) light, for example, in the treatment of cancerous growths or the like.

From U.S. Pat. No. 5,364,391, an optical fibre having a fingerpiece is known, wherein the fibre is inserted into a coupler and the other end of the fibre can be used for treatment. Often the fibres have special shapes or special features on their end opposite the connector, said special shapes or special features effecting lateral light radiation or the like, for example. As a result, these fibres are quite expensive.

Because the fibres are contaminated after the treatment, they cannot be reused, but must instead be disposed of. Attempts to sterilise strongly contaminated fibres have shown that it is not possible to achieve a sufficient germ-destruction rate within established times (3-5 minutes).

The object of the invention under consideration is therefore to create an optical fibre that allows a more economical solution.

This object is solved by an optical fibre according to claim 1 or 10.

Advantageous embodiments are disclosed in the dependent claims.

The optical fibre with a connector piece is formed in such a way that it can be easily cleaned and/or disinfected and/or sterilised. For example, devices that generate directed flows of a fluid are used for cleaning and/or disinfection and/or sterilisation by machine, in order to remove impurities and bacteria in this way. For this purpose, the optical fibres can, for example, be introduced into cleaning basins or cleaning chambers into which a cleaning fluid is circulated, sprayed or directed at the optical fibre in the form of a jet. It is also possible to fix the optical fibres in a particular position with the connector piece or a plug and to direct one or more targeted jets of cleaning fluid at the optical fibre, the connector piece or the plug.

Autoclaves are possible for cleaning and/or disinfection and/or sterilisation.

The optical fibre is accommodated in a connector piece. For this purpose, the connector piece has a recess, such as a central bore hole, for example. It is also possible to provide a depression on the connector piece at the position at which the optical fibre exits the connector piece. For example, this can be necessary when coupling the light from high-power light sources, in order to prevent destruction of the fibre in the coupling area.

At the end of the recess, meaning, for example, at the end of the bore hole, germs can easily collect between the optical fibre and the connector piece, but these germs can easily be removed by means of the fluid channel, which begins at the end of the recess and through which a fluid can move.

By means of an opening in a possible dead-end towards the back, it is possible to create a channel by means of which the dead-end is eliminated. Consequently, cleaning and/or disinfection and/or sterilisation is easily possible.

The fluid channel preferably runs a good part of the way along the optical fibre, as a result of which it is easily possible to clean and/or disinfect and/or sterilise the area along the optical fibre.

Furthermore, it is advantageous if the fluid channel exits to the side of the optical fibre, because then the entering cleaning fluid can be dispensed in a direction other than the direction from which, for example, a jet of fluid emerges with appropriate pressure. The deflection to the side furthermore has the advantage that the channel does not have to go through the entire connector piece, although this is also possible.

In order to avoid hollow spaces that are difficult to access, the connector piece is preferably glued and/or crimped to the fibre. The glued positions are preferably covered with an elastic sealing material, such as silicone or the like, for instance. Crimping provides a good hold between the fibre and the connector piece. If necessary, the crimping area can be additionally sealed using a glue.

For better handling, the optical fibre advantageously has a suitable gripping piece.

The gripping piece can, for example, be snapped to the connector piece. This allows a quite simple design.

An optical fibre can have a plug with a gripping piece that has two end openings, through which the optical path leads and that are interconnected in a way allowing throughflow. In this way, it is possible to prevent the formation of dead-ends, which facilitates cleaning and/or leads to a better possibility of disinfection and/or better possibility of sterilisation.

An optical fibre is shown in a three-dimensional, schematic sectional view in the accompanying figure.

The optical fibre 1 is provided with a plug shown in the figure. The optical fibre 1 has two areas 4, 5, wherein in area 4, the fibre 1 is surrounded with a protective sheath that has been removed in area 5. This protective sheath can be made of plastic, for example. The optical fibre 1 is formed in a continuous piece between the areas 4 and 5.

The optical fibre 1 with the areas 4, 5 is accommodated in a connector piece 3. The connector piece 3 has a central recess in the form of a bore hole, in which the optical fibre 1 is arranged and that has a larger diameter at one end than, for example, in the middle or at the other end. In this way, the area 4 of the optical fibre 1 with the protective sheath can be inserted into the connector piece 3 and, as a result, reach a limit stop, if the protective sheath hits upon the tapered portion of the central bore hole.

The area 5 of the optical fibre 1 ends flush with the connector piece 3 (at the right of the figure). The optical fibre 1 can, however, also project somewhat further or be somewhat recessed.

The connector piece 3 preferably possesses a depression 17 at the end of the area 5, so that the end of the area 5 stands somewhat free. This is advantageous for coupling to a high-power light source.

In section 7 (glue section) of the connector piece 3, the optical fibre 1 is glued to the connector piece 3. In section 6 (guide section), through which the optical fibre 1 with the area 5 goes, the area 5 is not glued. Because no gluing is provided here, the guide section 6 serves to accommodate the optical fibre 1 without there being a permanent connection. The optical fibre 1 is then only loosely guided by this section. When the optical fibre 5 has been inserted, a channel 18 surrounds it.

In section 7, the optical fibre can be connected to the connector piece by crimping or another mechanical connection.

The section 6 has openings 14 arranged on the side, next to the area 5 of the optical fibre 1. These can also be given by a single bore hole or milling going through the connector piece 3. Because the optical fibre 1 is not glued to the connector piece 3 in the area 5 in the section 6 of the connector piece 3, it is possible, for example, for cleaning fluid or steam to enter at the depression 17, to reach the opening 14 along the area 5 through the through hole 18 of the connector piece 3 and then exit again. In this way, a good possibility for cleaning and/or disinfection and/or sterilisation is given along this path. The cleaning fluid or steam can also flow in the reverse direction.

To improve the conveyance of the fluid along the optical fibre 1 in section 6, it is also possible to provide, on the interior of the through hole 18 of the connector piece 3, ribs 19, burls or similar spacing elements, that, while keeping the optical fibre 1 at a distance to the interior of the connector piece 3, nevertheless allow easy passage of the fluid through the channel 18 along the optical fibre 1. Such burls 19 are not absolutely necessary, however.

The glued section 7 of the connector piece 3 attaches to the opening 14. Because of the gluing that is done up to the opening 14, the formation of a dead-end, which could only be cleaned and/or disinfected and/or sterilised with difficulty, along the optical fibre 1 is avoided.

The openings 14 extend in the direction transverse to the optical fibre 1. Preferably, the two openings 14 are interconnected in a way allowing throughflow, so that a cleaning fluid or a flow of gas can enter into the connector piece 3 from the side through an opening 14, cross the optical fibre 1 through the connector piece 3 and then exit again through the opposite hole 14. In this way, good cleaning and/or the possibility of disinfection and/or the possibility of sterilisation is given.

At the end of the connector piece 3 shown to the left in the figure, an elastic sealing material, such as silicone 20 or an elastic glue can be provided, that encloses the optical fibre 1 that leaves from the connector piece 3, so that the area between the optical fibre 1 and the connector piece 3 is sealed. An elastic sealing material (silicone or the like) can also be provided for sealing at the position at which the optical fibre 1 leaves the connector piece 3 in the opening 14.

The connector piece 3 can additionally have a lateral opening 10, through which the glue 11a can be directed to the area 4 or 5, in order in this way to glue the optical fibre 1 to the connector piece 3 and to seal this lateral opening 10. The glue 11a can be pressed by means of appropriate pressure, starting from the opening 10 along the optical fibre 1 up to the opening 14 and to the end shown in the left of the figure, in order to achieve gluing of the optical fibre 1 to the glued section 7 over as much of the surface as possible.

The glue opening 10 can, for example be provided at that position at which the area 4 passes into the area 5. The opening 10 with glue therein is advantageously covered with an elastic sealing material 11b, such as silicone or the like, for example.

Covering of the glue with the elastic sealing material such as silicone or the like serves to seal any cracks in or at the glue. Cracks that may form in the glue or between the glue and the connector piece 3, such as, for example, can occur as the result of a heavy thermal load, would be disadvantageous for good cleaning and/or a good possibility of disinfection and/or a good possibility of sterilisation, because germs could collect there that could only be removed with difficulty. Therefore it is advantageous to seal the positions that come into question with an elastic sealing material 11b, 20. This is not as susceptible to thermal loads, because it is elastic and the expansions of the materials can adapt suitably to temperature changes.

The mechanical connection of the fibre 1 to the connector piece 3, for example by crimping, can also be sealed using the glue and/or the sealing material.

The connector piece 3 is accommodated in a gripping piece 2. The gripping piece 2 essentially has the form of a pipe 12 and has two end openings 15, 16. The optical fibre 1 enters with the area 4 through the end opening 15 and enters with the area 5 through the end opening 16. The connector piece 3 is connected to the gripping piece 2 via a partition wall 8. The partition wall 8 is formed in the manner of a circular disc and has a central opening for accommodating the connector piece 3.

In area 13, the connector piece 3 can be snapped together with the partition wall 8. For this purpose, the connector piece 3 has a groove-like depression, into which the partition wall 8 of the gripping piece 2 can be inserted for snapping. In this process, the gripping piece 2 is pushed from the left side of the figure to the right with one movement, along the optical fibre 1 over the connector piece 3. In order to make this easier, a tapered form is provided on the narrower end of the connector piece 3.

The snap-on connection between connector piece 3 and gripping piece 2 is advantageously arranged in such a way that the gripping piece 2 is permanently connected to the connector piece 3, i.e., it cannot simply be removed again. In this way, an accidental detachment of the gripping piece 2 is prevented. It is also possible, however, for a detachable gripping piece 2 to be provided, that is removed, for example, for cleaning and/or disinfection and/or sterilisation, in order to simplify cleaning and/or disinfection and/or sterilisation even further, because hollow spaces are largely avoided.

The central opening of the partition wall 8 has indentations 9, so that this central opening remains open even when the connector piece 3 has been inserted. In this way, the end openings 15, 16 of the gripping piece are interconnected in a way allowing throughflow and a flow of cleaning agent or gas is possible through the gripping piece 2 during cleaning and/or disinfection and/or sterilisation, in order to achieve good cleaning and/or disinfection and/or sterilisation results.

The optical fibre 1 shown in the figure can be inserted into a light source with the plug shown in the figure, so that light is coupled into the area 5, consequently providing an extension of the area 4 for treatment.

The gripping piece 2 preferably has a corresponding locking section with which the gripping piece 2 can be connected to a light source or also with which it can be positioned in a cleaning and/or disinfection and/or sterilisation device, such as an autoclave, for example. This locking section can, for example, comprise a Luer-Lock with a double-threaded thread.

The gripping piece 2 can have a corrugation, flattened areas or the like on its outer side, which facilitate the handling of the gripping piece 2 during traversing or rotating movements of the gripping piece 2.

The invention claimed is:

1. An optical fiber system, comprising:
   an optical fiber;
   a connector coupled to the optical fiber, the connector comprising
   a first bore within which at least a portion of the optical fiber is disposed,
   a first opening adjacent to the first bore,
   a second opening adjacent to the first bore, and
   a fluid channel connecting the first opening and the second opening, the fluid channel defining a path by which at least one of a fluid and a gas enters through the first opening, contacts at least a portion of the optical fiber, and exits through the second opening; and
   a tubular member surrounding at least a portion of the connector and at least a portion of the optical fiber, the tubular member comprising
   a first end comprising a third opening,
   a second end comprising a fourth opening, and
   a body connecting the first end and the second end, the body defining a second bore within which at least a portion of the connector is disposed, the body comprising a wall disposed within the second bore, the wall connecting the tubular member and the connector and defining at least one fifth opening that allows flow of at least one of a fluid and a gas through the tubular member, between the first end and the second end, substantially around the connector.

2. The optical fiber system of claim 1, wherein the second opening extends along a length of a side of the connector.

3. The optical fiber system of claim 2, wherein the first opening is disposed on an end of the connector.

4. The optical fiber system of claim 1, wherein the connector is crimped to the optical fiber.

5. The optical fiber system of claim 1, wherein the connector is glued to the optical fiber.

6. The optical fiber system of claim 5, wherein at least one exterior side of the glue is covered with an elastic sealing material.

7. The optical fiber system of claim 6, wherein the elastic sealing material comprises at least one of silicone and elastic glue.

8. The optical fiber system of claim 1, wherein the connector comprises a sixth opening adjacent to the first bore, the fluid channel connecting the first opening, the second opening, and the sixth opening,
wherein the path defined by the fluid channel allows the at least one of the fluid and the gas to exit through both the second opening and the sixth opening.

9. The optical fiber system of claim 8, wherein the second opening extends along a length of a first side of the connector and the sixth opening extends along a length of a second side of the connector, the first side being disposed opposite the second side.

10. The optical fiber system of claim 1, wherein the optical fiber extends through opposing ends of the connector.

11. The optical fiber system of claim 1, wherein the optical fiber extends through the third opening and the fourth opening.

12. The optical fiber assembly of claim 1, wherein each opening defined by the wall of the tubular member is defined by an indentation in the wall.

* * * * *